United States Patent
Xiang et al.

(10) Patent No.: US 8,653,264 B2
(45) Date of Patent: Feb. 18, 2014

(54) CRYSTAL OF ERLOTINIB BASE AND THE PREPARATION METHOD THEREOF

(75) Inventors: Ke Xiang, Zhejiang (CN); Min Xu, Zhejiang (CN)

(73) Assignee: Zhejiang Huahai Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 13/814,929

(22) PCT Filed: Aug. 12, 2011

(86) PCT No.: PCT/CN2011/078352
§ 371 (c)(1),
(2), (4) Date: Feb. 7, 2013

(87) PCT Pub. No.: WO2012/022240
PCT Pub. Date: Feb. 23, 2012

(65) Prior Publication Data
US 2013/0137867 A1    May 30, 2013

(30) Foreign Application Priority Data
Aug. 14, 2010    (CN) ............................ 201010258627

(51) Int. Cl.
*C07D 239/94*    (2006.01)

(52) U.S. Cl.
USPC .......................................... 544/293

(58) Field of Classification Search
USPC .......................................... 544/293
See application file for complete search history.

(56) References Cited

U.S. PATENT DOCUMENTS 5,747,498 A    5/1998    Schnur et al.
6,900,221 B1   5/2005    Norris et al.

FOREIGN PATENT DOCUMENTS

| CN | 101547910 A | 9/2009 |
| CN | 101602734 A | 12/2009 |
| CN | 101735157 A | 6/2010 |
| CN | 101914068 A | 8/2010 |
| WO | WO 2008012105 A1 | 1/2008 |
| WO | WO 2009024989 A2 | 2/2009 |

OTHER PUBLICATIONS

International Search Report dated Nov. 3, 2011 from corresponding International Application No. PCT/CN2011/078352.

*Primary Examiner* — Kristin Vajda
(74) *Attorney, Agent, or Firm* — Wolf, Greenfield & Sacks, P.C.

(57) ABSTRACT

A novel crystal of antitumor drug erlotinib base and its preparation method are provided in the present invention. A preparation method of erlotinib hydrochloride with high-purity is also provided in the present invention.

9 Claims, 5 Drawing Sheets

CRYSTAL OF ERLOTINIB BASE AND THE PREPARATION METHOD THEREOF

The present application claims the priority of China Patent Application No. 201010258627.9, filed with the China Patent Office on Aug. 14, 2010, titled "Novel crystal of erlotinib base and the preparation method thereof", the entire contents of which are incorporated herein by reference.

FIELD OF THE INVENTION

The present invention relates to the field of medicinal chemistry, particularly to a novel crystal form of erlotinib base and the preparation method thereof.

BACKGROUND OF THE INVENTION

Erlotinib hydrochloride is marketed in the United States for the first time in 2004, and is applicable for local advanced or metastatic non-small cell lung cancer. The chemical name of erlotinib base (or referred to as erlotinib) is N-(3-ethynylphenyl)-6,7-bis(2-methoxyethoxy)quinazolin-4-amine, and the structural formula thereof is shown below:

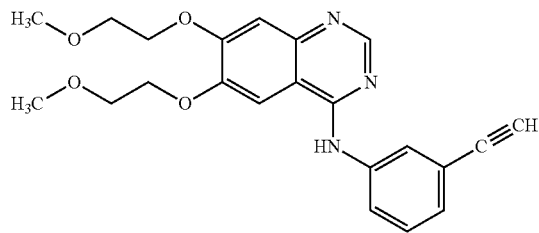 [SMILES: C#Cc1cccc(Nc2ncnc3cc(OCCOC)c(OCCOC)cc23)c1]

U.S. Pat. No. 5,747,498 reported the synthetic method of erlotinib hydrochloride for the first time, Example 20 therein mentioned using flash silica gel column to separate and purify crude erlotinib base, followed by transforming it into its hydrochloride salt. The method of silica gel purification used in this patent is difficult to be applied in industrial production.

U.S. Pat. No. 6,900,221 reported obtaining the crystal form A or a mixture of crystal form A and B of erlotinib nib hydrochloride by direct reaction between 4-chloro-6,7-bis-(2-methoxyethoxy)-quinazoline and 3-aminophenylacetylene in the mixture of toluene and acetonitrile, and it is difficult to purify the product by methods of further recrystallization due to the very low solubility of erlotinib hydrochloride.

WO2008012105 mentioned the crystal Form I, Form II, Form III of erlotinib base, their pharmaceutical composition and their use in the treatment of cancer, wherein Form I and Form III are in form of hydrate and Form II is in form of non-hydrate. The Form I reported in this patent requires higher water content, so that a mixed crystalline of Form I and Form II is easily obtained during the preparation process, and Form II and Form III are obtained by air drying organic solvents containing erlotinib base at room temperature and ambient condition, so that they can not be applied in industrialized production.

WO2009024989 mainly described a novel hydrate crystal form of erlotinib base (water content: 1-10%), however, in viewing of XRD of this hydrate, what actually obtained is a mixed crystal of Form I and Form II, so that a crystal form with high purity can not be obtained.

SUMMARY OF THE INVENTION

The purpose of the present invention is to provide a stable, novel crystal form of erlotinib base with high purity, which can be suitable for industrialized production.

In one aspect of the present invention, a novel crystal form IV of erlotinib base is provided, the 20 characteristic peaks in the X-ray powder diffraction pattern are located at 8.26±0.2, 9.16±0.2, 10.36±0.2, 10.80±0.2, 12.90±0.2, 17.80±0.2, 21.32±0.2, 24.08±0.2, 25.02±0.2 and 28.82±0.2 degree. The X-ray powder diffraction pattern of Form IV is shown in FIG. 1 (wherein allowable measurement error range is "±0.2").

The characteristic peaks of infrared (IR) absorption spectrum of Form IV are located at 740, 769, 946, 1052, 1073, 1098, 1245, 1333, 1361, 1448, 1513 and 3265 $cm^{-1}$. The IR spectrum of Form IV is shown in FIG. 2.

The DSC scanning of Form IV shows that the melting point is located in 132.37-137.46° C. The DSC scanning spectrum is shown in FIG. 3.

The present invention further provides a method for preparing the crystal form IV of erlotinib base, characterized in that crude erlotinib base is crystallized in a solvent system comprising a solvent selected from ethyl formate, butyl acetate or isopropyl acetate. Preferably, the crystallization is performed in a solvent system comprising ethyl formate.

Wherein, the Example 20 of compound patent WO 1996030347 can be referred to for the preparation method of crude erlotinib base.

The solvent system here can be completely or essentially consisted of any one or more solvents selected from ethyl formate, butyl acetate or isopropyl acetate; preferably, one or more additional cosolvents are added based on the above-mentioned ester solvents, wherein the cosolvent being selected from methanol, ethanol, isopropanol, n-butanol, tetrahydrofuran, 2-methyl tetrahydrofuran, acetonitrile and DMF.

Generally, when the cosolvent is not added, the amount of the ester solvent used is preferably 10-80 ml with respect to 1 g crude erlotinib base; where the cosolvent is added, the amount of the ester solvent used is preferably 1-40 ml with respect to 1 g crude erlotinib base, the amount of the cosolvent with respect to the crude erlotinib base is preferably 1-5 ml.

The general procedure for preparing the crystal form IV of erlotinib base is as follows:
(a) mixing crude erlotinib base with the solvent, and heating to dissolve the crude erlotinib base;
(b) cooling to room temperature with stirring, continue cooling to 0-5° C. to allow precipitation;
(c) separating and drying to obtain crystal form IV of erlotinib base.

The method for preparing crystal form IV of erlotinib base provided by the present invention employs esters of low toxicity as solvents, and the preparation method is safe, simple, operable, easy to be industrialized, and a pure crystal form is obtained. Form IV did not significantly change in the hygroscopicity experiment and the stability experiment, which is advantageous for the pharmaceutical applications of the novel crystal forms.

The preparation process of the crystal form IV of erlotinib base of the present invention is also a purifying process of erlotinib base, erlotinib hydrochloride with high purity can be obtained through further acidification using a hydrochloric acid solution. Said hydrochloric acid solution is selected from alcohol solution of hydrochloride, ether solution of hydrochloride and ester solution of hydrochloride.

The present invention further provides a process for preparing crystal form A of erlotinib hydrochloride with high purity, comprising the following steps:
(a) dissolving form IV of erlotinib base in an organic solvent selected from isopropanol, ethyl formate or dioxane,
(b) performing reaction by introducing isopropanol solution of hydrochloride,
(c) filtering and drying to obtain crystal form A of erlotinib hydrochloride.

The X-ray powder diffraction pattern and the IR absorption spectrum of form A of the present invention are shown in FIG. 4 and FIG. 5, respectively.

The method for preparing erlotinib hydrochloride provided by the present invention is easy to operate, and a product with high purity can be obtained.

DETAILED DESCRIPTION OF THE INVENTION

Figure 1:
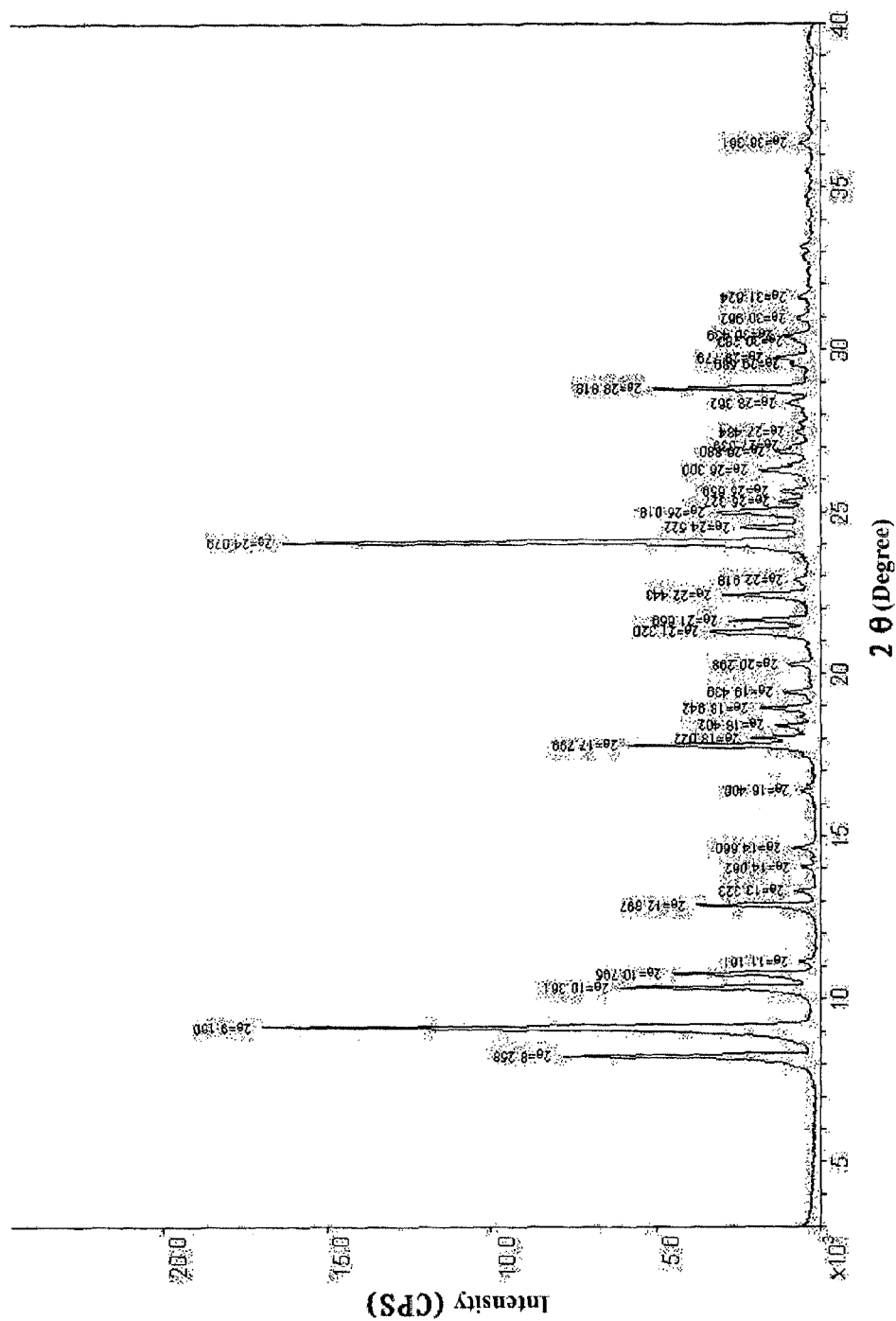
FIG. 1 is the X-ray powder diffraction pattern of the crystal form IV of erlotinib base provided by the present invention.
Figure 2:
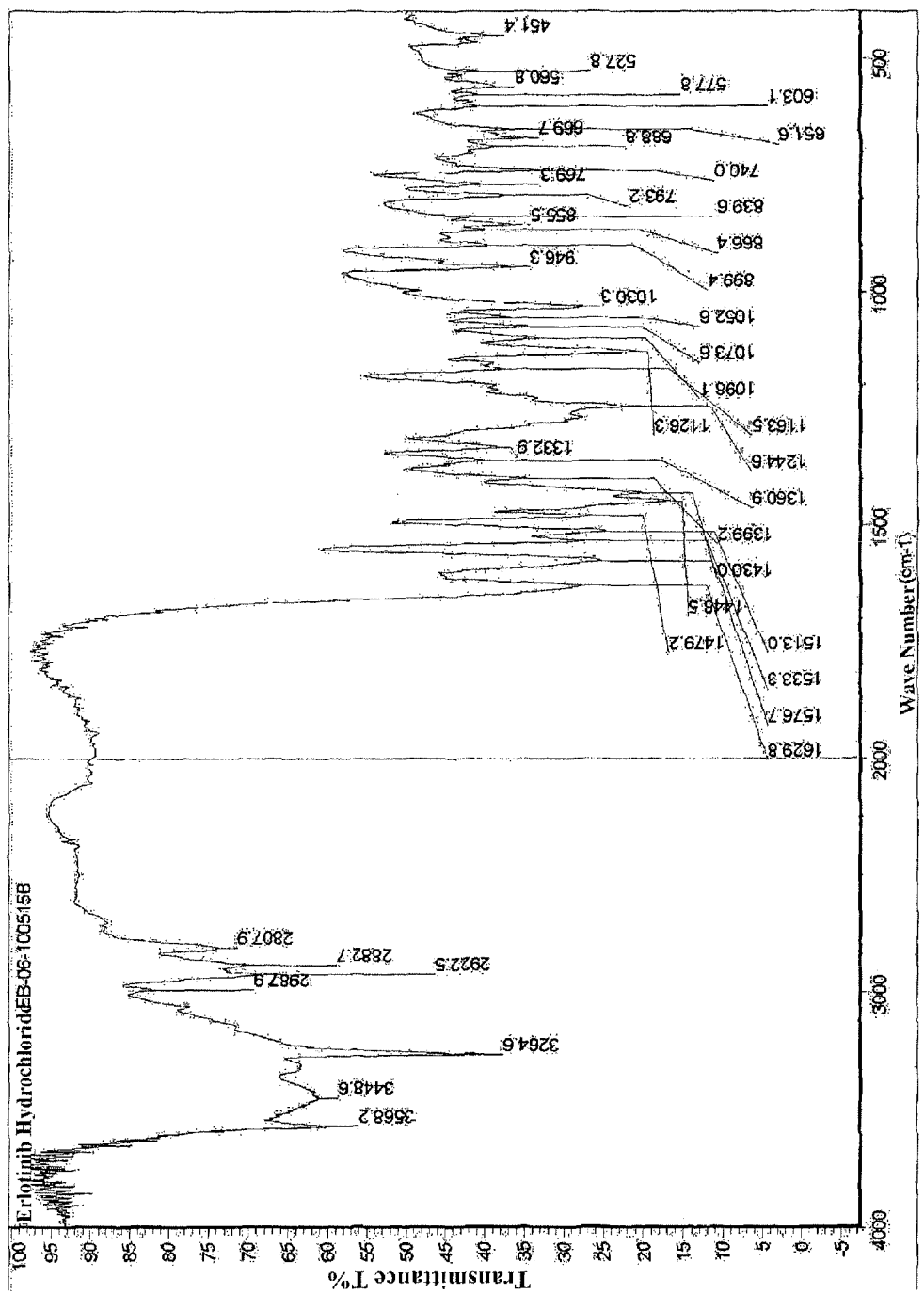
FIG. 2 is the IR spectrum of the crystal form IV of erlotinib base provided by the present invention.
Figure 3:
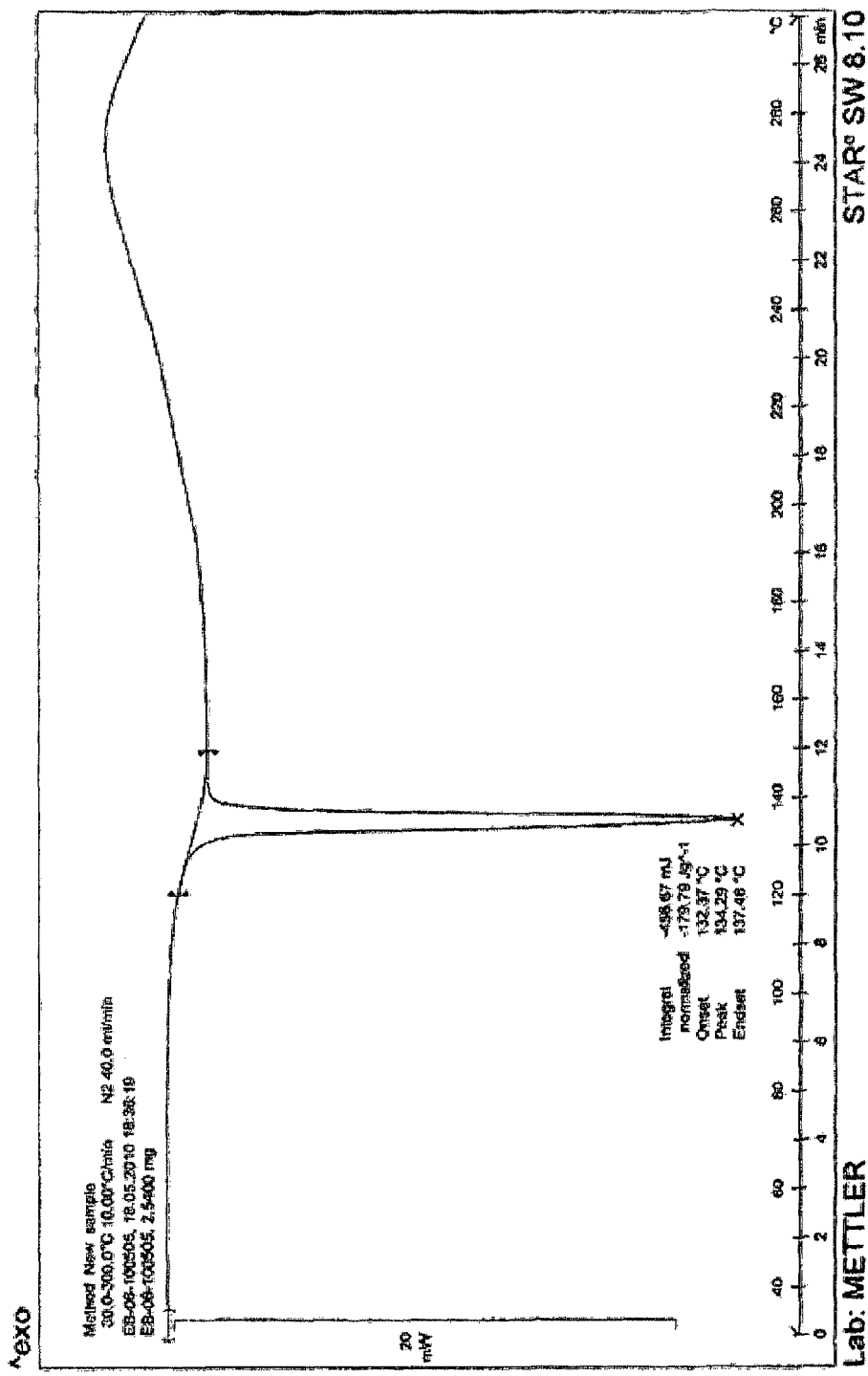
FIG. 3 is the DSC spectrum of the crystal form IV of erlotinib base provided by the present invention.
Figure 4:
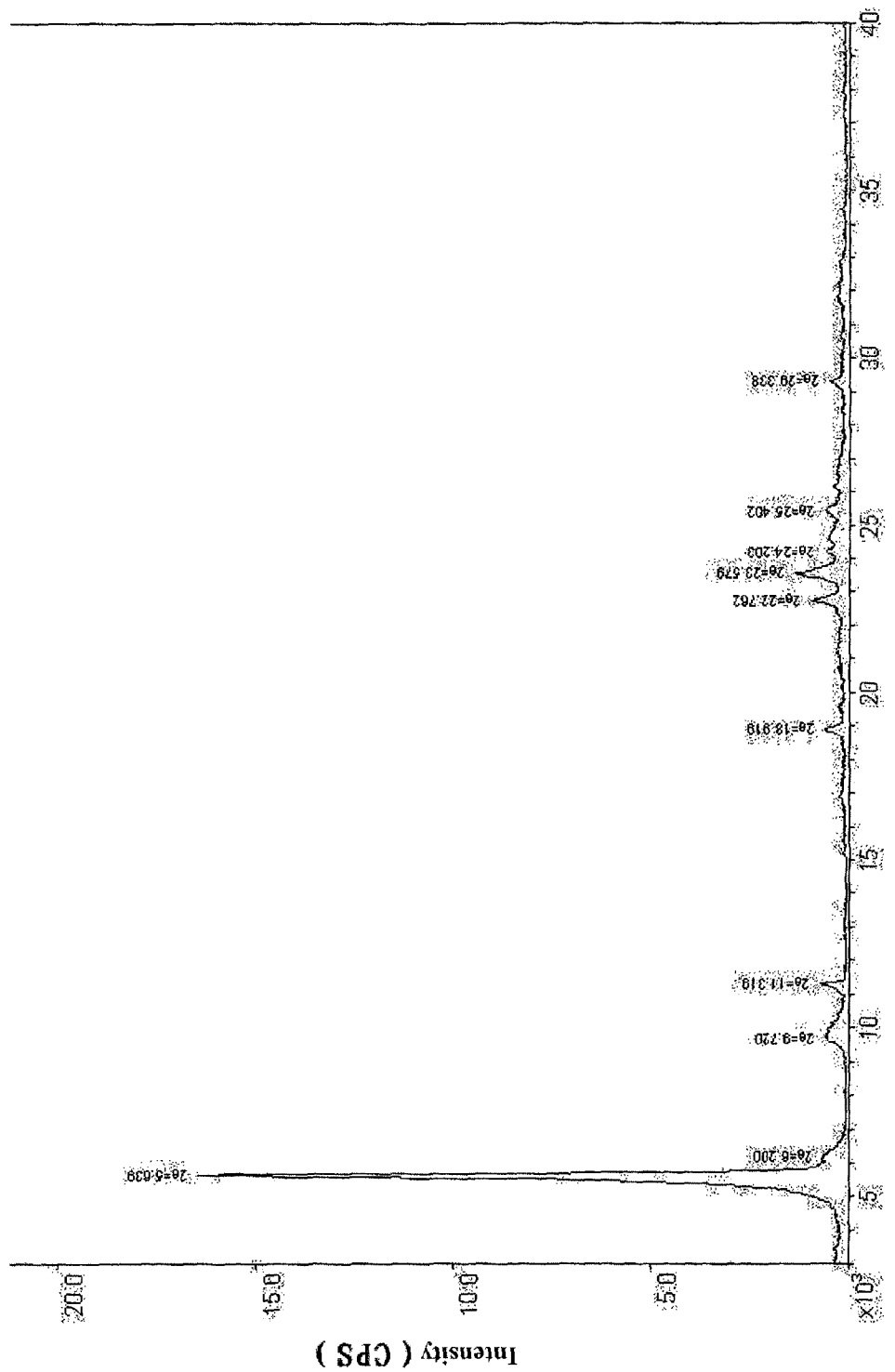
FIG. 4 is the X-ray powder diffraction pattern of the crystal form Form A of erlotinib hydrochloride provided by the present invention.
Figure 5:
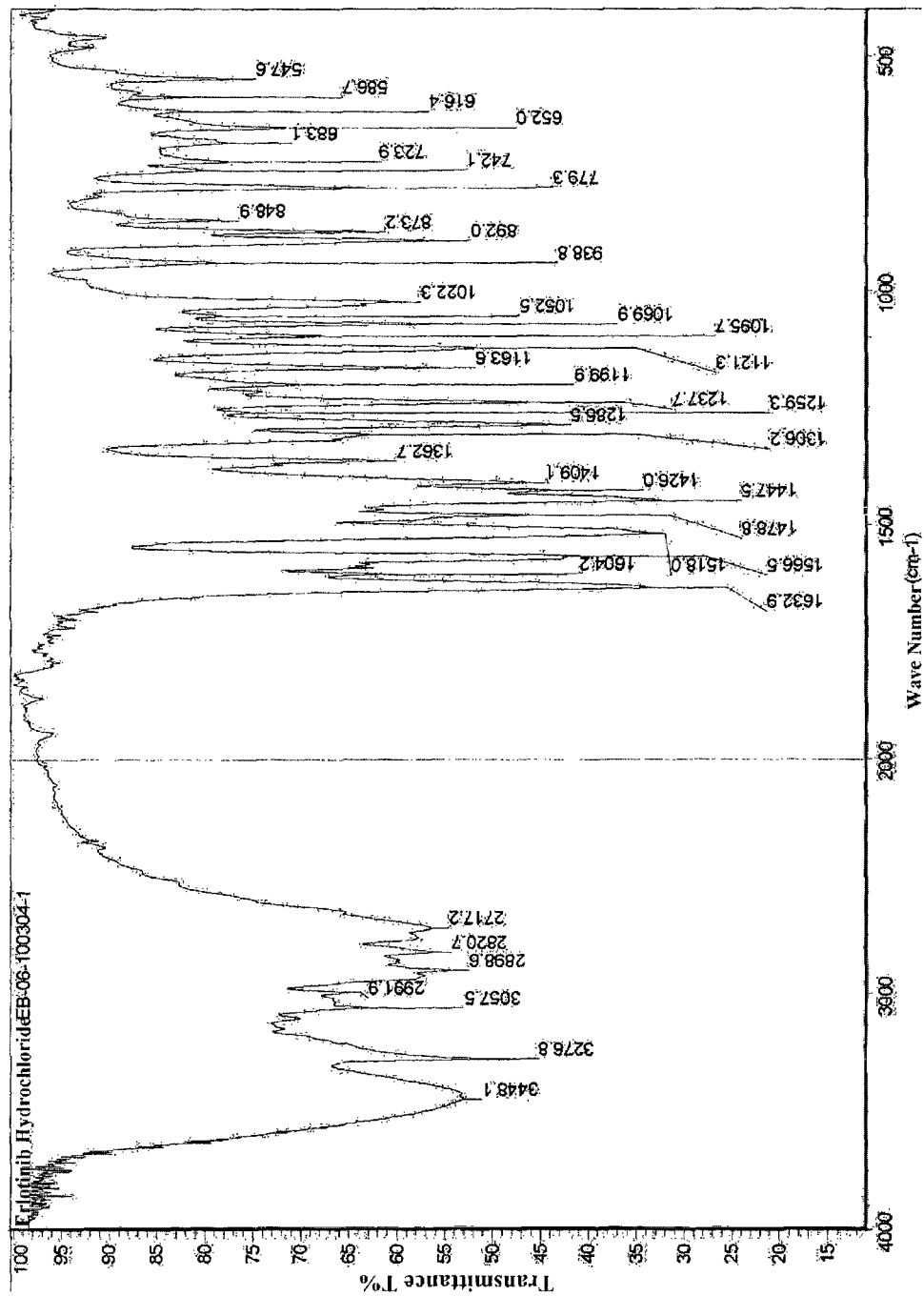
FIG. 5 is the IR spectrum of the crystal form Form A of erlotinib hydrochloride provided by the present invention.

In order to further illustrate the present invention, the preferred embodiments of the present invention will be described in association with the examples, however, it should be appreciated that these descriptions are only provided for further illustrating the features and advantages of the present invention, and are not to limit the claims of the present invention.

The effects of the present invention will be illustrated in the following specific Examples; however, the scope of protection of the present invention will not be limited to the following examples.

The X-ray powder diffraction pattern is recorded under the following conditions:
Detecting instruments: rotating anode target 12 KW X-ray polycrystalline spectrometer D/max-2500pc.
Detecting basis: JY/T009-1996.
Environmental conditions for the detection: indoor temperature 20° C.; relative humidity <60%.
Light source: Cu Kα ray,
Slit: DS: 1°, SS: 1°, Rs: 0.15 mm, Rsm: 0.8 mm.
Scanning range 2θ (°): 10°-50.0°.
Scanning mode: stepping.
Scanning step length: 0.02°.
Accumulated time: 0.5 s/step.
Tube potential: 40 kv.
Tube current: 250 mA.
Rear graphite monochromator, data processing Jade 7.0 software package.
IR spectrum is recorded under the following conditions:
Detecting instruments: Nicolet 380
Detecting method: potassium bromide tabletting method
DSC spectrum is recorded under the following conditions:
Detecting instruments: METTLER DSC 822
Detecting method: aluminum crucible, under nitrogen purging, heating rate: 10° C./min, scan from 50° C. to 250° C.

Example 1

Preparation of Crystal Form IV of Erlotinib Base 10.0 g erlotinib was added to 500 ml ethyl formate, and heated to 54° C. to reflux for 30 minutes. Hot filtration was performed to remove insoluble. Then cooled to room temperature with stirring, and further cooled to 0-5° C., stirred for 1 hour before filtration, dried at 50° C. to obtain 9.0 g sample of crystal form IV. The yield was 90.0% and the purity was 99.7% (by HPLC).

Example 2

Preparation of Crystal Form IV of Erlotinib Base 10.0 g erlotinib was added to 300 ml ethyl formate and 10 ml methanol, and heated under reflux until all of the solid has been dissolved, then cooled to room temperature with stirring, and further cooled to 0-5° C., stirred for 1 hour before filtration, dried at 50° C. to obtain 8.5 g sample of crystal form IV. The yield was 85.0% and the purity was 99.8% (by HPLC).

Example 3

Preparation of Crystal Form IV of Erlotinib Base 10.0 g erlotinib was added to 300 ml ethyl formate and 10 ml n-butanol, and heated under reflux until all of the solid has been dissolved, then cooled to room temperature with stirring, and further cooled to 0-5° C., stirred for 1 hour before filtration, dried at 50° C. to obtain 8.6 g sample of crystal form IV. The yield was 86.0% and the purity was 99.6% (by HPLC).

Example 4

Preparation of Crystal Form IV of Erlotinib Base 10.0 g erlotinib was added to 300 ml ethyl formate and 10 ml tetrahydrofuran, and heated under reflux until all of the solid has been dissolved, then cooled to room temperature with stirring, and further cooled to 0-5° C., stirred for 1 hour before filtration, dried at 50° C. to obtain 8.5 g sample of crystal form IV. The yield was 85.0% and the purity was 99.5% (by HPLC).

Example 5

Preparation of Crystal Form IV of Erlotinib Base 10.0 g erlotinib was added to 300 ml ethyl formate and 10 ml 2-methyl tetrahydrofuran, and heated under reflux until all of the solid has been dissolved, then cooled to room temperature with stirring, and further cooled to 0-5° C., stirred for 1 hour before filtration, dried at 50° C. to obtain 8.7 g sample of crystal form IV. The yield was 87.0% and the purity was 99.5% (by HPLC).

Example 6

Preparation of Crystal Form A of Erlotinib Hydrochloride 10.0 g crystal form IV of erlotinib base was added to 250 ml isopropanol, heated to obtain a clear solution, 6.4 g saturated hydrochloric acid gas solution in isopropanol was added dropwise at 60-70° C., after dripping, stirred for 30 minutes while maintaining the temperature, then cooled the temperature to 10-15° C., stirred for 1 hour before filtration, dried at 50° C. to obtain 10.2 g sample of crystal form A. The yield was 93.6% and the purity was 99.7% (by HPLC).

Example 7

Preparation of Crystal Form A of Erlotinib Hydrochloride 10.0 g crystal form IV of erlotinib base was added to 200 ml ethyl formate, heated to 0-10° C., 6.4 g isopropanol saturated with HCl gas was added dropwise, after dripping, stirred for 30 minutes while maintaining the temperature, stirred for 1 hour at 0-15° C. before filtration, dried at 50° C. to obtain 10.2 g sample of crystal form A. The yield was 93.6% and the purity was 99.7% (by HPLC).

Example 8

Preparation of Crystal Form A of Erlotinib Hydrochloride 10.0 g crystal form IV of erlotinib base was added to 200 ml 1,4-dioxane, heated to dissolve until being clarified, 6.4 g isopropanol saturated with HCl gas was added dropwise at 60-70° C., after dripping, stirred for 30 minutes while maintaining the temperature, stirred for 1 hour at 0-15° C. before filtration, dried at 50° C. to obtain 10.6 g sample of crystal form A. The yield was 97.2% and the purity was 99.8% (by HPLC).

A novel crystal form of erlotinib base and the preparation method thereof proposed by the present invention have been described through Examples. It is apparent for those skilled in the art that changes or appropriate alterations and combinations can be made to the novel crystal form of erlotinib base and the preparation method thereof described herein without departing the content, spirit and scope of the present invention, to achieve the techniques of the present invention. It should be particularly pointed out that all the similar alterations and changes are apparent to those skilled in the art, and are regarded to be included within the spirit, scope and content of the present invention.

The invention claimed is:

1. A crystal form IV of erlotinib base, characterized in that, the values of 2θ characteristic peaks in the X-ray powder diffraction pattern of the crystal form are located at 8.26±0.2, 9.16±0.2, 10.36±0.2, 10.80±0.2, 12.90±0.2, 17.80±0.2, 21.32±0.2, 24.08±0.2, 25.02±0.2 and 28.82±0.2 degree.

2. The crystal form IV of erlotinib base according to claim 1, characterized in that the characteristic peaks of IR absorption spectrum of the crystal form IV are located at 740, 769, 946, 1052, 1073, 1098, 1245, 1333, 1361, 1448, 1513 and 3265 cm$^{-1}$.

3. A method for preparing the crystal form IV of erlotinib base according to claim 1, characterized in that crude erlotinib base is crystallized in a solvent system comprising a solvent selected from ethyl formate, butyl acetate or isopropyl acetate.

4. The method according to claim 3, wherein the solvent system is ethyl formate.

5. The method according to claim 3, characterized in that the solvent system further comprises one or more cosolvents, said cosolvent being selected from methanol, ethanol, isopropanol, n-butanol, tetrahydrofuran, 2-methyl tetrahydrofuran, acetonitrile and DMF.

6. The method according to claim 3, characterized in that the method comprises the following steps:
 (a) mixing the crude erlotinib base with the solvent system, and heating to dissolve the crude erlotinib base;
 (b) cooling to room temperature with stirring, continue cooling to 0-5° C. to allow precipitation;
 (c) separating and drying to obtain crystal form IV of erlotinib base.

7. A method for preparing erlotinib hydrochloride with high purity, comprising treating the crystal form IV of erlotinib base obtained according to claim 3 with a hydrochloric acid solution.

8. The method according to claim 7, wherein the hydrochloric acid solution is selected from alcohol solution of hydrochloride, ether solution of hydrochloride and ester solution of hydrochloride.

9. A method for preparing erlotinib hydrochloride with high purity, comprising the following steps:
 (a) dissolving form IV of erlotinib base of claim 1 in an organic solvent selected from the group consisting of isopropanol, ethyl formate, and dioxane,
 (b) performing reaction by introducing an isopropanol solution of hydrochloride,
 (c) filtering and drying to obtain crystal form A of erlotinib hydrochloride.

* * * * *